United States Patent
Kölbel et al.

(10) Patent No.: US 10,675,140 B2
(45) Date of Patent: *Jun. 9, 2020

(54) INTRODUCER FOR DEPLOYING A STENT GRAFT IN A CURVED LUMEN AND STENT GRAFT THEREFOR

(71) Applicant: Cook Medical Technologies LLC, Bloomington, IN (US)

(72) Inventors: Tilo Kölbel, Hamburg (DE); Erik E. Rasmussen, Slagelse (DK); Bent Oehlenschlaeger, Lille Skensved (DK); Kim Moegelvang Jensen, Frederiksberg (DK)

(73) Assignee: Cook Medical Technologies LLC, Bloomington, IN (US)

( * ) Notice: Subject to any disclaimer, the term of this patent is extended or adjusted under 35 U.S.C. 154(b) by 246 days.

This patent is subject to a terminal disclaimer.

(21) Appl. No.: 15/839,115

(22) Filed: Dec. 12, 2017

(65) Prior Publication Data

US 2018/0110610 A1 Apr. 26, 2018

Related U.S. Application Data

(63) Continuation of application No. 12/609,066, filed on Oct. 30, 2009, now Pat. No. 9,855,128.

(30) Foreign Application Priority Data

Oct. 31, 2008 (GB) .................................. 0820061.0

(51) Int. Cl.
*A61F 2/07* (2013.01)
*A61F 2/95* (2013.01)
*A61F 2/89* (2013.01)

(52) U.S. Cl.
CPC .................. *A61F 2/07* (2013.01); *A61F 2/95* (2013.01); *A61F 2/89* (2013.01);
(Continued)

(58) Field of Classification Search
CPC .............. A61F 2/06–07; A61F 2/95–97; A61F 2002/061–077; A61F 2002/9505–9665
See application file for complete search history.

(56) References Cited

U.S. PATENT DOCUMENTS

| 4,878,906 A | 11/1989 | Lindemann et al. |
| 4,913,141 A | 4/1990 | Hillstead |

(Continued)

FOREIGN PATENT DOCUMENTS

| JP | 2006-346350 | 12/2006 |
| WO | WO 01/74270 A2 | 10/2001 |

(Continued)

OTHER PUBLICATIONS

Canadian Office Action and Search Report for CA Application No. 2,737,438 dated Aug. 25, 2015, 3 pages.
(Continued)

*Primary Examiner* — Jonathan A Hollm
(74) *Attorney, Agent, or Firm* — Brinks Gilson & Lione

(57) ABSTRACT

A stent graft for deployment in a curved lumen such as the aortic or thoracic arch comprises a constraining mechanism at its proximal end. A stent provided at the proximal end of the stent graft includes loops of material that co-operate with restraining wires that extend between a central guide wire carrier and a restraining wire cannula. The constraining mechanism maintains the proximal stent constrained at both of its proximal and distal ends. The proximal stent can then expand after expansion of the remainder of the stent graft during deployment. In an embodiment, the constraining mechanism acts to constrain two adjacent struts of the proximal stent at three points radially therearound, at the proximal end of the stent and at the distal end of the stent. The proximal stent may then overlap with the interior of an adjacent stent at an inner part of a curved vessel.

18 Claims, 11 Drawing Sheets

(52) U.S. Cl.
CPC ........... *A61F 2002/9505* (2013.01); *A61F 2002/9511* (2013.01); *A61F 2002/9517* (2013.01); *A61F 2230/0067* (2013.01)

(56) References Cited

U.S. PATENT DOCUMENTS

| | | | |
|---|---|---|---|
| 5,693,083 | A | 12/1997 | Baker et al. |
| 5,843,158 | A | 12/1998 | Lenker et al. |
| 6,562,064 | B1 | 5/2003 | deBeer |
| 6,692,521 | B2 | 2/2004 | Pinchasik |
| 6,964,677 | B2 | 11/2005 | Osypka |
| 7,160,318 | B2 | 1/2007 | Greenberg et al. |
| 7,611,528 | B2 | 11/2009 | Goodson, IV et al. |
| 7,803,177 | B2 | 9/2010 | Hartley et al. |
| 7,909,863 | B2 | 3/2011 | Hartley et al. |
| 9,220,617 | B2 | 12/2015 | Berra |
| 2001/0041925 | A1 | 11/2001 | Konya et al. |
| 2002/0007208 | A1 | 1/2002 | Strecker |
| 2003/0050684 | A1 | 3/2003 | Abrams et al. |
| 2003/0233140 | A1 | 12/2003 | Hartley et al. |
| 2004/0073289 | A1 | 4/2004 | Hartley |
| 2004/0106978 | A1 | 6/2004 | Greenberg et al. |
| 2004/0138734 | A1 | 7/2004 | Chobotov et al. |
| 2004/0193178 | A1 | 9/2004 | Nikolchev |
| 2004/0193244 | A1 | 9/2004 | Hartley et al. |
| 2004/0220655 | A1 | 11/2004 | Swanson et al. |
| 2005/0085890 | A1 | 4/2005 | Rasmussen et al. |
| 2005/0090887 | A1 | 4/2005 | Pryor |
| 2005/0107862 | A1 | 5/2005 | Ohlenschlaeger |
| 2005/0119722 | A1 | 6/2005 | Styrc |
| 2005/0137701 | A1 | 6/2005 | Salahieh et al. |
| 2005/0288768 | A1 | 12/2005 | Sowinski et al. |
| 2006/0142836 | A1 | 6/2006 | Hartley et al. |
| 2006/0190070 | A1 | 8/2006 | Dieck et al. |
| 2007/0100427 | A1 | 5/2007 | Perouse |
| 2007/0208409 | A1 | 9/2007 | Quigley |
| 2007/0233223 | A1 | 10/2007 | Styrc |
| 2008/0027529 | A1 | 1/2008 | Hartley et al. |
| 2008/0077226 | A1 | 3/2008 | Ouellette |
| 2008/0140178 | A1 | 6/2008 | Rasmussen et al. |
| 2008/0243225 | A1 | 10/2008 | Satasiya |
| 2009/0030497 | A1 | 1/2009 | Metcalf et al. |
| 2009/0082842 | A1 | 3/2009 | Glynn |
| 2009/0082847 | A1 | 3/2009 | Zacharias |
| 2009/0099640 | A1 | 4/2009 | Weng |
| 2009/0112302 | A1 | 4/2009 | Stafford |
| 2009/0171431 | A1 | 7/2009 | Swanson et al. |
| 2009/0204202 | A1 | 8/2009 | Dierking et al. |
| 2009/0259291 | A1 | 10/2009 | Kolbel et al. |
| 2010/0010617 | A1 | 1/2010 | Goodson, IV et al. |
| 2010/0168838 | A1 | 7/2010 | Hartley et al. |
| 2010/0249896 | A1 | 9/2010 | Sugimoto et al. |
| 2010/0286768 | A1 | 11/2010 | Alkhatib |
| 2011/0178588 | A1 | 7/2011 | Haselby |
| 2011/0190865 | A1 | 8/2011 | McHugo et al. |
| 2011/0288624 | A1 | 11/2011 | Roeder et al. |
| 2012/0010696 | A1 | 1/2012 | Greenberg et al. |
| 2012/0277848 | A1 | 11/2012 | Roeder et al. |
| 2013/0245743 | A1 | 9/2013 | Norris |

FOREIGN PATENT DOCUMENTS

| | | |
|---|---|---|
| WO | WO 2004/017868 A1 | 3/2004 |
| WO | WO 2006/037086 A1 | 4/2006 |
| WO | WO 2009/126227 A2 | 10/2009 |

OTHER PUBLICATIONS

European International Search Report and Written Opinion for European Application No. PCT/US2009/005890, dated Feb. 4, 2010, 9 pages.

Extended European Search Report dated Apr. 4, 2013, European Patent Application 12197088.3, European Patent Office, The Netherlands, 7 pages.

English translation of Japanese Office Action/Reason for Rejection for JP 2011-534517, dated Aug. 27, 2013, 2 pages.

Office Action for U.S. Appl. No. 13/970,861, dated Jun. 4, 2015, 11 pages.

Response to Office Action for U.S. Appl. No. 13/970,861, dated Oct. 5, 2015, 9 pages.

Office Action for U.S. Appl. No. 13/713,517, dated Mar. 16, 2015, 20 pages.

Response to Office Action for U.S. Appl. No. 13/713,517, dated Sep. 16, 2015, 9 pages.

INTRODUCER FOR DEPLOYING A STENT GRAFT IN A CURVED LUMEN AND STENT GRAFT THEREFOR

RELATED APPLICATIONS

This application is a continuation of U.S. application Ser. No. 12/609,066, filed Oct. 30, 2009, which claims priority to United Kingdom Patent Application No. 0820061.0, filed Oct. 31, 2008 entitled "Introducer For Deploying a Stent Graft in a Curved Lumen and Stent Graft Therefor." This application is related to United Kingdom Patent Application No. 0820066.9, filed Oct. 31, 2008

FIELD OF THE INVENTION

The present application relates to an introducer for deploying a stent graft within a curved lumen. It also relates to a stent graft for deployment within a curved lumen.

BACKGROUND

Stent grafts are used to replace or repair vessels of the body such as arteries. A stent graft is usually formed from a tubular body of a biocompatible graft material with one or more stents mounted into or onto the tubular body to provide support therefore. The stents may be balloon expandable stents or self-expanding stents.

Endovascular methods have been proposed for treatment of aneurysms of the aorta particularly where the aneurysm is adjacent the aorta bifurcation. However, when an aneurysm occurs higher up in the aorta, in the region of the descending aorta adjacent the aortic or thoracic arch or in the ascending aorta, endovascular techniques for treating these aneurysms are somewhat more difficult because of the tight curvature of the aortic or thoracic arch, the occurrence of major arteries in the region and the proximity to the heart. Placement of a substantially cylindrical prosthesis in such a curved region can cause problems.

Stent grafts are typically deployed using endovascular techniques on an introduction device in which the stent graft is retained in a radially contracted condition by a sheath. Upon withdrawal of the sheath and release of any retention arrangement where provided, for example in cases in which the stent graft has self-expanding stents, the stent graft can expand under the action of the self-expanding stents towards the vessel walls to redefine the blood flow path. The introduction device is withdrawn after deployment.

Currently, stent grafts are deployed in curved lumens by causing these to follow the curvature imparted to the introducer. However, this can result in the stent graft not sitting properly in the blood vessel and in the lumen of the prosthesis being closed off or reduced in lumen diameter.

Furthermore, when deploying a stent graft that is substantially straight in a curved aorta there is a danger that the proximal end of the stent graft, that is, the end nearest the heart, will not lie flat against the walls of the aorta (i.e., the end "face" is not positioned perpendicularly to the wall of the vessel) and blood can flow underneath the edge of the graft, particularly on the inner side of the curve of the aortic or thoracic arch and cause the stent graft to buckle and close off thereby causing serious problems.

FIGS. 1 and 2 illustrate this problem. The introducer and stent graft generally have a substantially straight configuration but as a result of their pliancy are urged into a curved orientation by the walls of the lumen. However, as the stent graft is held on the introducer, which itself tends to maintain its straightened configuration to the extent that it keeps to the outside of the curve of the lumen, the stent graft also tends to maintain a lesser curved configuration as it is being deployed. When the stent graft is released from its ties to the introducer, it expands in a manner which continues to tend to the straightened configuration and in particular to push the inner edge of the stent graft forwardly. This leads to an increased Proximal Face Angle (PFA), that is, to an increased angle between the line formed by the proximal end of the stent graft and the line perpendicular to the walls of the lumen. It also leads to an increased Proximal Normal Gap (PNG), that is, a gap between the lumen wall and the proximal end of the stent on the inner part of the bend in the lumen. These are shown in FIGS. 1 and 2. The Proximal Normal Gap allows blood pressure to build between the outside of the stent graft and the lumen wall, which will tend to bias this side of the stent graft inwardly into the lumen and thus towards closing of the lumen of the stent graft. Thus, the seal at the proximal end of the stent graft may not be as effective as desired. This gap can also cause the graft material itself to flap in the fluid flow, leading to unnatural fluid flow and possible premature wear and tear of the stent graft.

US 2004/0073289 discloses a stent graft for deployment within a curved portion of the aorta.

SUMMARY

The subject matter of the present application seeks to provide an improved introducer and method for deploying a stent graft within a curved lumen, as well as a stent graft for deployment in a curved lumen.

In general the teachings herein relate to the placement of prostheses in the aorta in the region known as the aortic or thoracic arch, where the aorta leaves the heart and curves in approximately a U-shape to the descending aorta, then into the abdominal aorta and then into the lower limbs via the iliac arteries. The teachings herein are, however, not so restricted and can relate to placement of prostheses within or in place of lumens in any portion of a human or animal body, though it is particularly relevant to curved lumens.

According to an aspect of the present invention, there is provided an introducer for deploying a stent graft in a curved lumen, the introducer including: a carrier for a stent graft, which stent graft is provided with a plurality of stents including a proximal stent at a proximal end of the stent graft; a release mechanism including a constraining mechanism operable to maintain the proximal stent of the stent graft in a constrained configuration at at least two points during deployment whilst allowing at least a portion of the stent graft distal of the proximal stent to expand; wherein the constraining mechanism is operable to constrain both the proximal end and the distal end of the proximal stent at said at least two points.

This arrangement ensures that the proximal-most stent of the stent graft can be kept constrained during deployment, allowing the rest of the stent graft to expand and permitting the proximal stent to expand thereafter, so as to enable the proximal end of the stent graft to be positioned substantially perpendicularly to the vessel wall prior to its expansion. In particular, this arrangement can promote overlap of graft material just distal of the distal end of the proximal stent and thus a better curvature of the stent graft. As a result, it is possible to achieve an improved seal between the proximal stent and the vessel wall.

Thus, in an embodiment, the release mechanism is operable to enable the constrained stent to expand so as to overlap with the interior of at least a portion of a distally adjacent stent in the expanded portion of the stent graft. This helps the stent graft conform to curved vasculature.

In a preferred embodiment, the release mechanism is operable to constrain the proximal stent at at least two, preferably three, points during deployment. In an embodiment, the at least two points are substantially evenly spaced radially around the proximal stent.

The release mechanism preferably includes at least one restraining wire able to hold loops of thread provided on an implantable medical device so as to constrain the implantable medical device to the introducer. The at least one restraining wire is preferably located within a lumen of the carrier of the introducer.

The introducer may include a center guide wire carrier provided within the lumen of the carrier. The carrier may be provided with a plurality of apertures therein for receiving the loops of thread of the implantable medical device.

The introducer preferably includes at least three restraining wires. It may include at least six restraining wires.

According to another aspect of the present invention, there is provided a stent graft for deployment in a curved lumen, the stent graft arranged to be deployed by an introducer as described above, wherein the stent graft is provided with a mechanism for allowing at least two points of the proximal stent to be constrained during deployment whilst a portion of the stent graft is expanded, wherein the at least two points of the proximal stent are able to be constrained at both the proximal end of the stent and at the distal end of the stent.

According to another aspect of the present invention, there is provided a stent graft for deployment in a curved lumen, including an element of graft material providing an inner lumen, a plurality of stents located longitudinally along the graft element, at least one of said stents being a proximal stent located at a proximal end of the stent graft, a plurality of loops of thread located at or adjacent proximal and distal ends of the proximal stent and extending into the inner lumen, wherein the plurality of loops are able to allow at least two points of the proximal stent to be constrained during deployment whilst a portion of the stent graft is expanded, wherein the loops provided at the at least two points of the proximal stent are able constrain both the proximal and the distal ends of the stent.

As such, the stent graft can provide an improved seal at its proximal end, because the proximal stent can be located substantially perpendicularly to the vessel wall prior to expansion.

In a preferred embodiment, the mechanism allows the proximal stent to be constrained at three points during deployment.

Preferably, the at least two points are substantially evenly spaced radially around the proximal stent.

Preferably the constraining mechanism is operable to constrain the distal end of the proximal stent substantially entirely therearound.

In an embodiment, the constraining mechanism is operable to constrain at least two adjacent struts of the proximal stent to the introducer at each of the at least two points of the proximal stent.

The loops are preferably substantially evenly spaced around the circumference of the proximal stent.

The portions of the loops extending into the inner lumen may be located at or adjacent junctions of two adjoining struts forming the proximal stent.

There may be provided a plurality of threads of material for forming the loops. There may be provided a single length of thread providing said plurality of loops.

According to another aspect of the present invention, there is provided an assembly including an introducer for deploying a stent graft in a curved lumen, the introducer including a carrier for a stent graft, which stent graft is provided with a plurality of stents including a proximal stent at a proximal end of the stent graft; a release mechanism including a constraining mechanism operable to maintain the proximal stent of the stent graft in a constrained configuration at at least two points during deployment whilst allowing at least a portion of the stent graft distal of the proximal stent to expand; wherein the constraining mechanism is operable to constrain both the proximal end and the distal end of the proximal stent at said at least two points; the assembly including a stent graft, the stent graft including: an element of graft material providing an inner lumen, a plurality of stents located longitudinally along the graft element, at least one of said stents being a proximal stent located at a proximal end of the stent graft, a plurality of loops of thread located at or adjacent proximal and distal ends of the proximal stent and extending into the inner lumen, wherein the plurality of loops are able to allow at least two points of the proximal stent to be constrained during deployment whilst a portion of the stent graft is expanded, wherein the loops provided at the at least two points of the proximal stent are able constrain both the proximal and the distal ends of the stent.

Preferably the loops are able to constrain the distal end of the proximal stent substantially entirely therearound.

In an embodiment, the mechanism includes at least one wire-receiver for co-operating with a release wire of the introducer. The wire-receiver may be a loop of material, such as a suture loop.

The term thread as used herein is intended to include any filamentary material which can perform the stated function and could, for example, be of conventional suture material, a multi-filamentary structure formed of yarns for example and of a natural or synthetic material such as cotton, other biocompatible material or a polymer material such as polyester, or a mono-filamentary structure of a natural material, other biocompatible material, a metal such as gold or an alloy such as Nitinol.

BRIEF DESCRIPTION OF THE DRAWINGS

Embodiments of the present invention are described below, by way of example only, with reference to the accompanying drawings, in which.

DETAILED DESCRIPTION OF THE PREFERRED EMBODIMENTS

It is to be understood that the Figures are schematic and do not show the various components to their actual scale. In many instances, the Figures show scaled up components to assist in understanding their structures and functions.

In this description, when referring to a deployment assembly, the term distal is used to refer to an end of a component which in use is furthest from the surgeon during the medical procedure, including within a patient. The term proximal is used to refer to an end of a component closest to the surgeon and in practice in or adjacent an external manipulation part of the deployment or treatment apparatus.

On the other hand, when referring to an implantable medical device such as a stent or stent graft, the term proximal refers to a location which in use is closest to the patient's heart, in the case of a vascular implant, and the term distal refers to a location furthest from the patient's heart.

Figure 3:
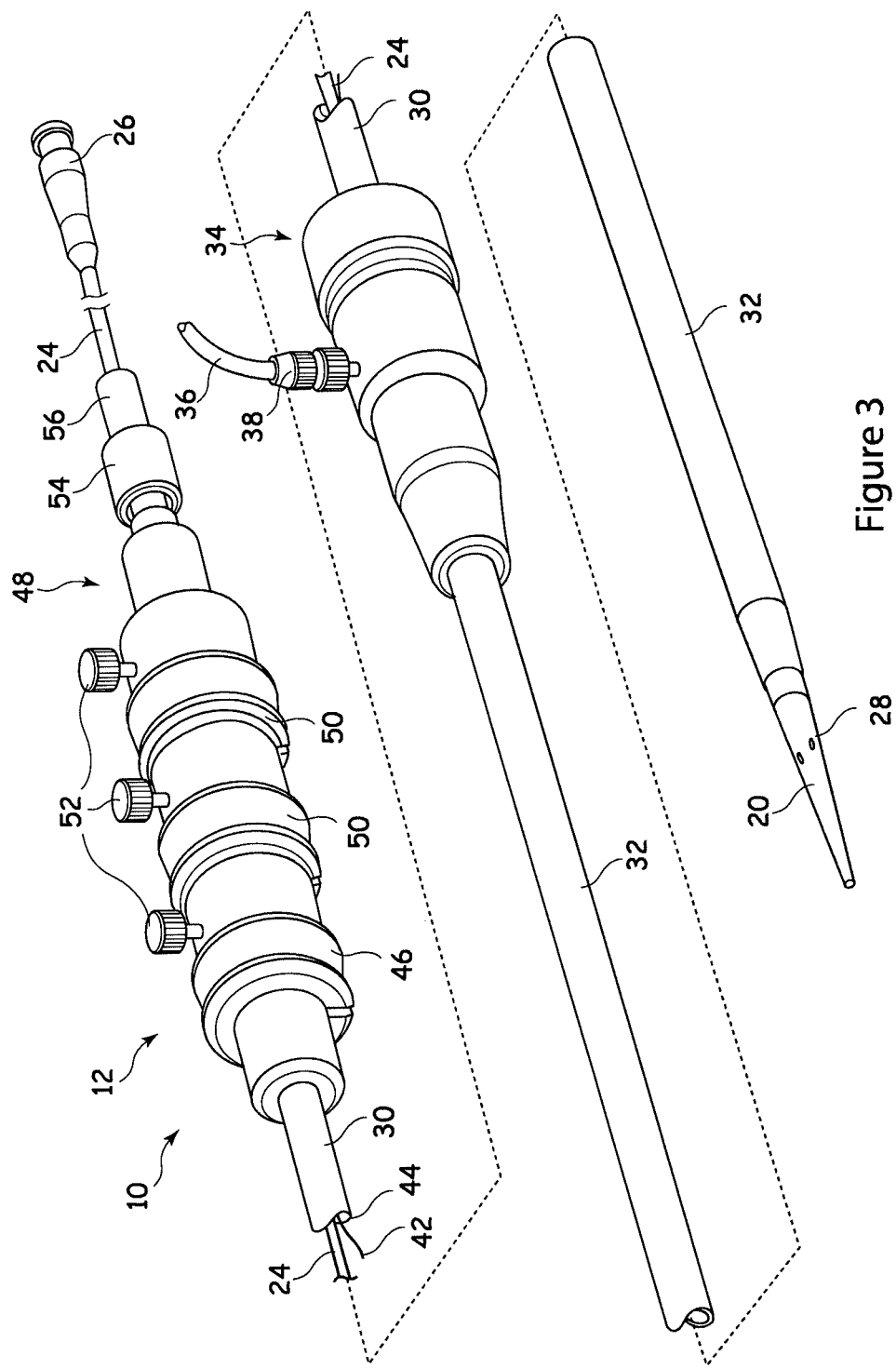
FIGS. 3 and 4 show an example of an implant deployment device that can be used with the teachings herein.
Figure 4:
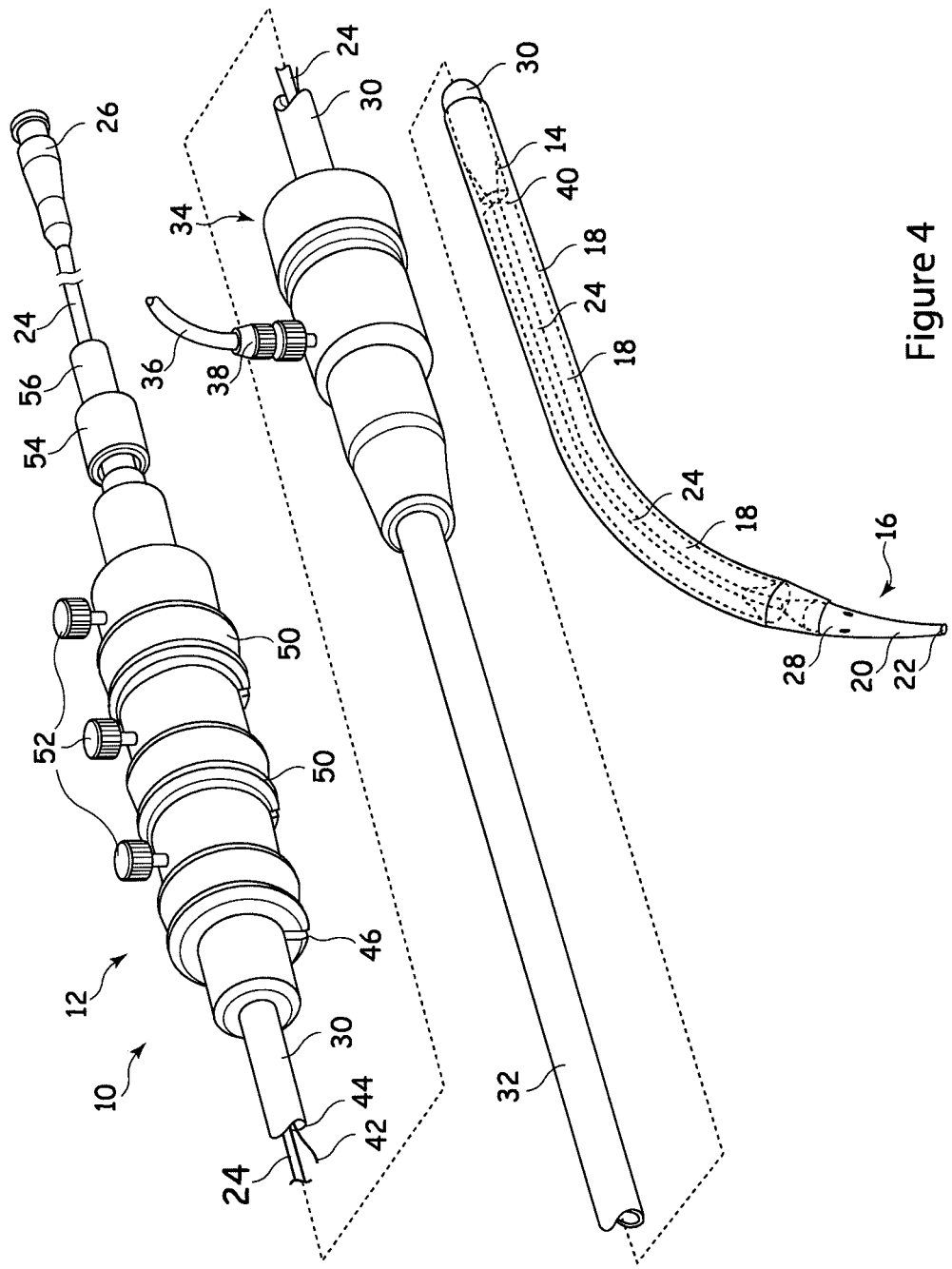

Referring to FIGS. 3 and 4, an implant deployment device 10 includes an external manipulation section 12, a proximal attachment region 14 and a distal attachment region 16. The proximal attachment region 14 and the distal attachment region 16 secure the two ends of the implant 18. During the medical procedure to deploy the implant 18, the proximal and distal attachment regions 14 and 16 will travel through the patient's vasculature, in this example, to a desired deployment site. The external manipulation section 12 at the proximal end of the implant deployment device 10, which is operated by a surgeon to manipulate the introducer, remains outside of the patient throughout the procedure.

The distal attachment region 16 of the implant deployment device 10 includes a dilator tip 20, which is typically provided with a bore 22 therein for receiving a guide wire (not shown) of conventional type. The longitudinal bore 22 also provides a channel for the introduction of medical reagents. For example, it may be desirable to supply a contrast agent to allow angiography to be performed during placement and deployment phases of the medical procedure.

A guide wire carrier or cannula 24, conventionally made from a flexible thin walled metal tube, is fastened to the dilator tip 20. The guide wire carrier 24 is flexible so that the implant deployment device 10 can be advanced along a relatively tortuous vessel, such as a femoral artery, and so that the distal end of the implant deployment device 10 can be longitudinally and rotationally manipulated. The guide wire carrier 24 carries a stent 18 or other device to be implanted in the patient. The guide wire carrier 24 extends through the implant deployment device 10 to the manipulation section 12, terminating at a connection device 26, in conventional manner.

The connection device 26 is designed to accept a syringe to facilitate the introduction of reagents into the guide wire carrier 24 and for this purpose is typically provided with a threaded luer lock connection.

Where provided, a pusher sheath or rod 30 (hereinafter referred to as a pusher member), typically made from a plastics material, is mounted coaxial with and radially outside of the guide wire carrier 24. The pusher member 30 is "thick walled", that is the thickness of its wall is preferably several times greater than that of the guide wire carrier 24. In some instances, the pusher member 30 and the guide wire carrier 24 are the same component, possibly having different outer diameters at the location at which the stent 18 is to be carried.

A sheath 32 extends coaxially over and radially outside of the pusher member 30. The pusher member 30 and the sheath 32 extend distally to the manipulation region 12.

The implant 18, which is a stent graft, is retained in a compressed condition by the sheath 32. The sheath 32 extends proximally to a sheath manipulator and haemostatic sealing unit 34 of the external manipulation section 12. The haemostatic sealing unit 34 includes a haemostatic seal (not shown) and a side tube 36 held to the unit 34 by a conventional luer lock 38.

The sheath manipulator and haemostatic sealing unit 34 also includes a clamping collar (not shown) that clamps the sheath 32 to the haemostatic seal and a silicone seal ring (not shown) that forms a haemostatic seal around the pusher member 30. The side tube 38 facilitates the introduction of medical fluids between the pusher member 30 and the sheath 32. Saline solution is typically used.

Figure 1:
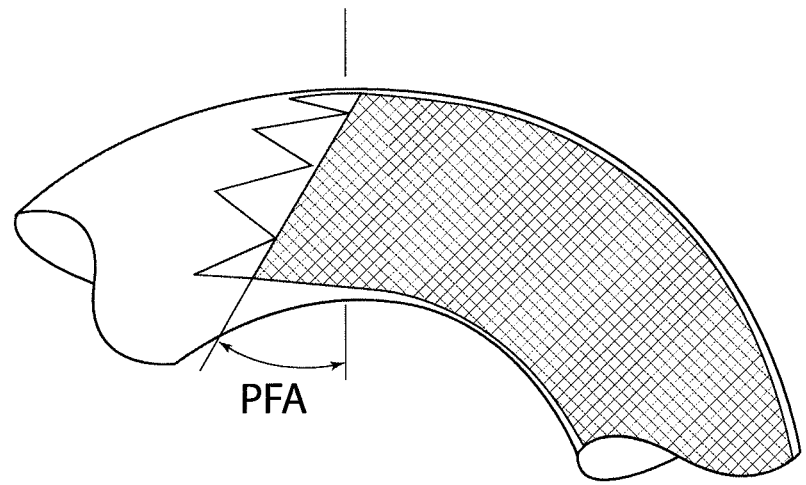
FIGS. 1 and 2 are schematic illustrations of problems with deployment of a stent graft in a curved lumen.
Figure 2:
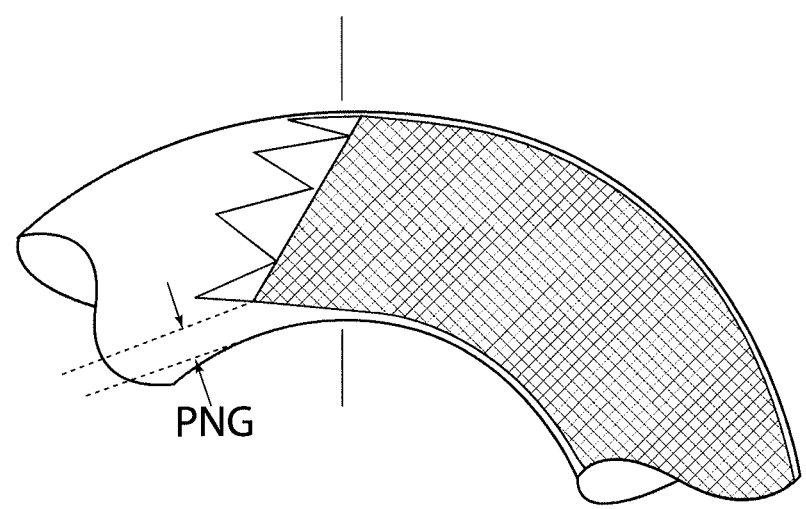

During assembly of the implant deployment device 10, the sheath 32 is advanced over the proximal end of the dilator tip 20 of the proximal attachment region 16 while the implant 18 is held in a compressed state by an external force. A suitable distal attachment (retention) section (not visible in this view) is coupled to the pusher member 30 and retains a distal end 40 of the prosthesis 18 during the procedure. The distal end of the prosthesis 18 may be provided with a loop of material (not shown) through which a distal restraining wire 42 extends. The distal restraining wire also extends through an aperture (not shown in FIGS. 1 and 2) in the proximal attachment section 40 into an annular region 44 between the guide wire carrier 24 and the pusher member 30. The distal restraining wire 42 extends through the annular space 44 to the manipulation region 12 and exits the annular space 44 at a distal wire release mechanism 46.

A proximal portion of the external manipulation section 12 includes at least one restraining wire actuation section 50 mounted on a body 48, in turn mounted onto the pusher member 30. The guide wire carrier 24 passes through the body 48. The distal wire release mechanism 46 and the proximal wire release mechanism 50 are mounted for slidable movement on the body 48.

Clamping screws 52 prevent inadvertent early release of the prosthesis 18. A haemostatic seal (not shown) is included so that the release wires can extend out through the body 48 without unnecessary blood loss during the medical procedure.

A proximal portion of the external manipulation section 12 includes a pin vise 54 mounted onto the proximal end of the body 48. The pin vise 54 has a screw cap 56. When screwed in, vise jaws (not shown) of the pin vise 54 clamp against or engage the guide wire carrier 24. When the vise jaws are engaged, the guide wire carrier 24 can only move with the body 48 and hence it can only move with the pusher member 30. With the screw cap 56 tightened, the entire assembly can be moved together as one piece.

Once the implant deployment device 10 is in the desired deployment position, the sheath 32 is withdrawn and the proximal and distal wire release mechanisms 50, 46 are released to allow the prosthesis 18 to expand.

For some procedures, the sheath 32 may be left in place after expansion of the implant 18. The pusher member 30 and guide wire carrier 24 may be withdrawn and replaced by a further component, using the sheath 32 as a guide.

It is to be understood that the guide wire carrier 24 can sometimes be described, both above and in the description which follows, as a center guide wire carrier, as a cannula or as a sheath and in all of the embodiments described herein it could take any of these forms. It is also to be understood that although some embodiments described below make use of a guide wire carrier as well as an introducer carrier, this is not an essential combination as it is envisaged that in some embodiments a guide wire may be carried within the carrier of the introducer, that is without any separate guide wire carrier or cannula.

Figure 5:
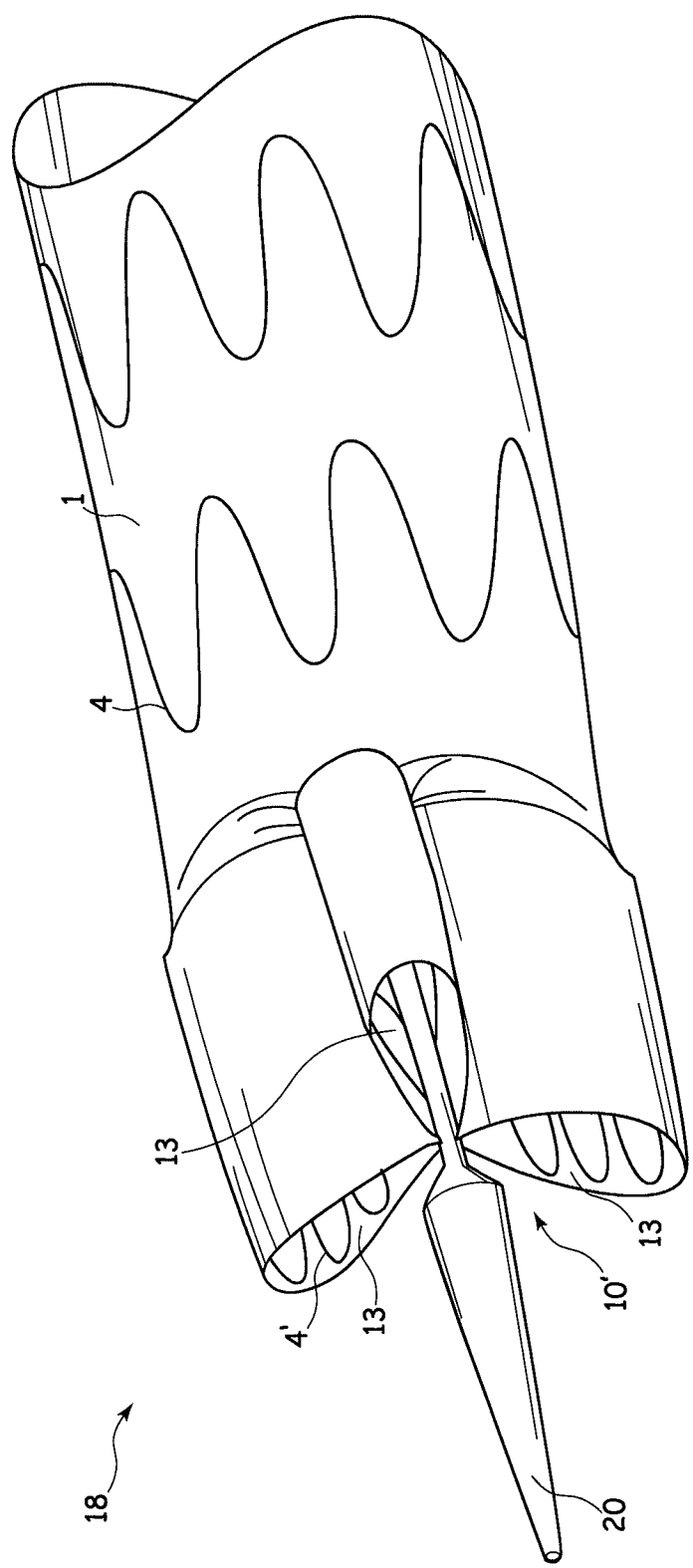
FIG. 5 shows a perspective view of an embodiment of a stent graft mounted on a deployment device.
Figure 6:
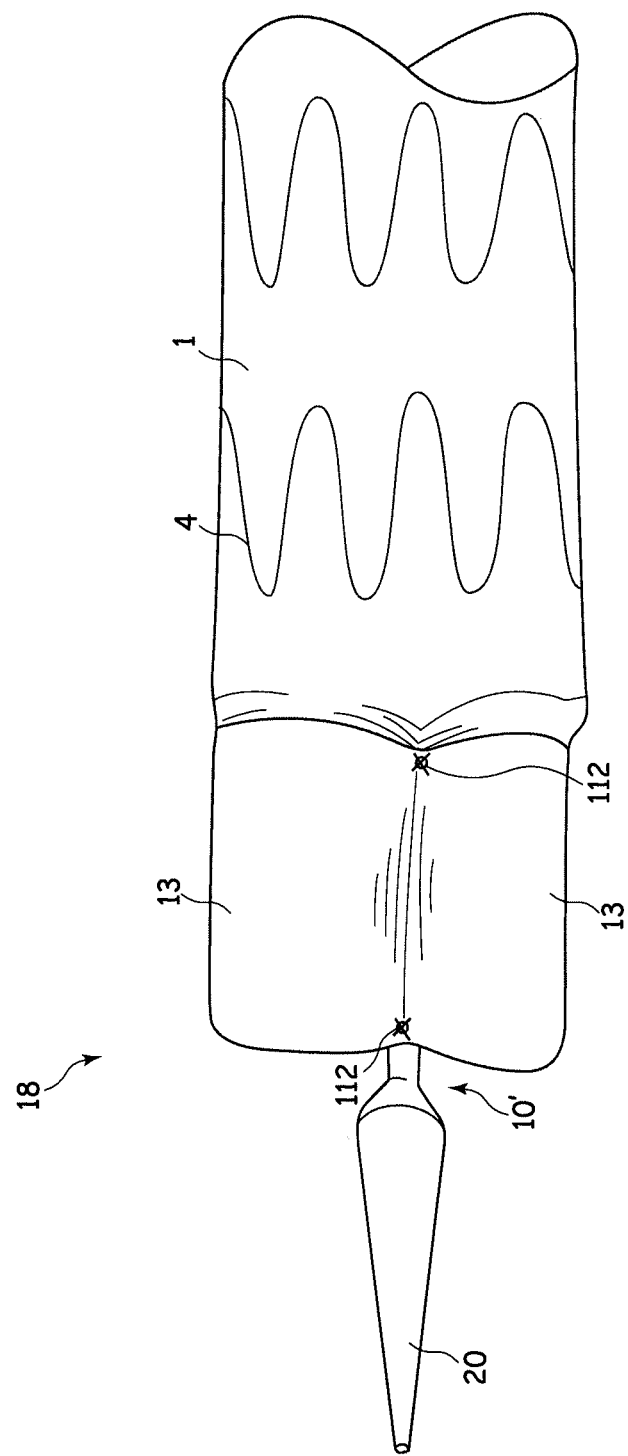
FIG. 6 shows a top view of the stent graft and deployment device of FIG. 5.
Figure 7:
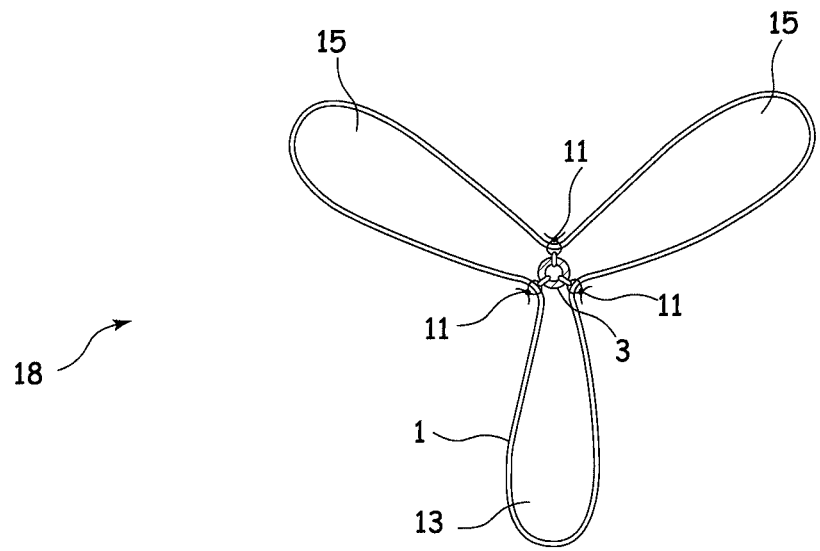
FIG. 7 shows a transverse cross-section through a portion of the stent graft and deployment device of FIG. 5.

FIGS. 5 to 7 illustrate an embodiment of stent graft 18, shown mounted on an introducer 10', which may be of the type illustrated in FIGS. 3 and 4. The stent graft 18 is formed from a tubular element of biocompatible graft material 1 provided with a plurality of stents 4, 4' disposed along its length, the example shown including Z-stents. In this embodiment, the stent 4' located at the proximal end of the tubular piece of graft material 1 is disposed on the inside of the tube 1, whereas other stents 4 are located outside the tube 1. In other embodiments, the various stents can be positioned differently with respect to the inside and outside of the tube and can also be all on the same side.

The most proximal stent 4' is provided, at substantially equally spaced locations therearound, with three loops of suture material 11 at its proximal end and three loops of suture material 11 at its distal end. The loops of suture material 11 are, in this embodiment, threaded through the graft material 1 and around a strut of the stent 4'. Other arrangements may be envisaged in other embodiments.

The loops of suture material 11 are able to engage with a release wire 42 of the introducer 10' to form a constraining mechanism for use during deployment of the stent graft 18. The constraining mechanism serves to constrain the proximal stent 4' on the deployment device 10' at, in this embodiment, three positions around its circumference, resulting in the creation of three lobes 13 of graft material 1 at the proximal end of the stent graft. The purpose of this is described below.

Figure 8:
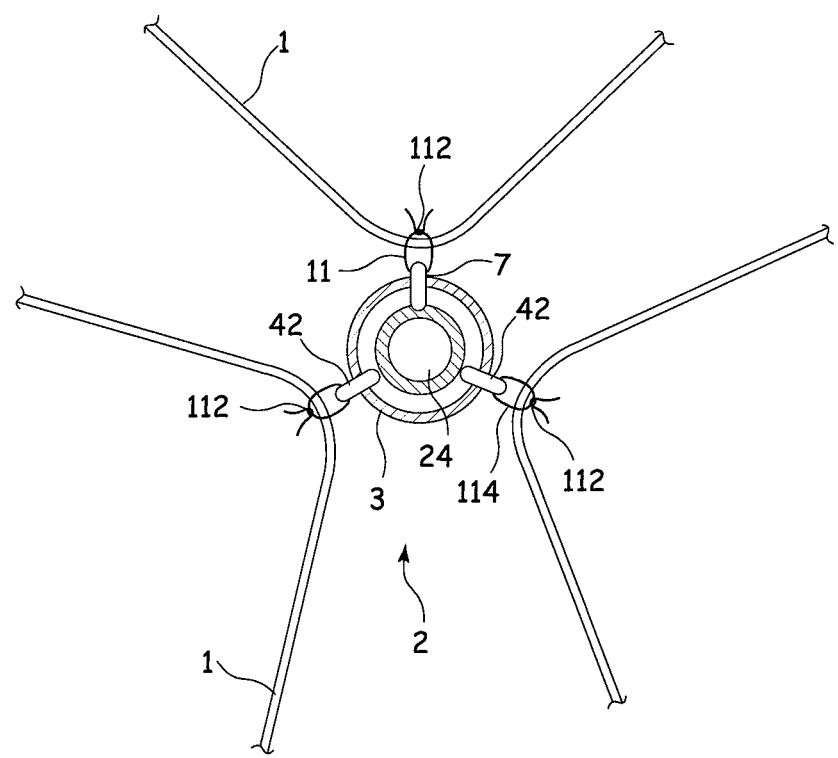
FIG. 8 shows an enlargement of a part of FIG. 7.
Figure 9:
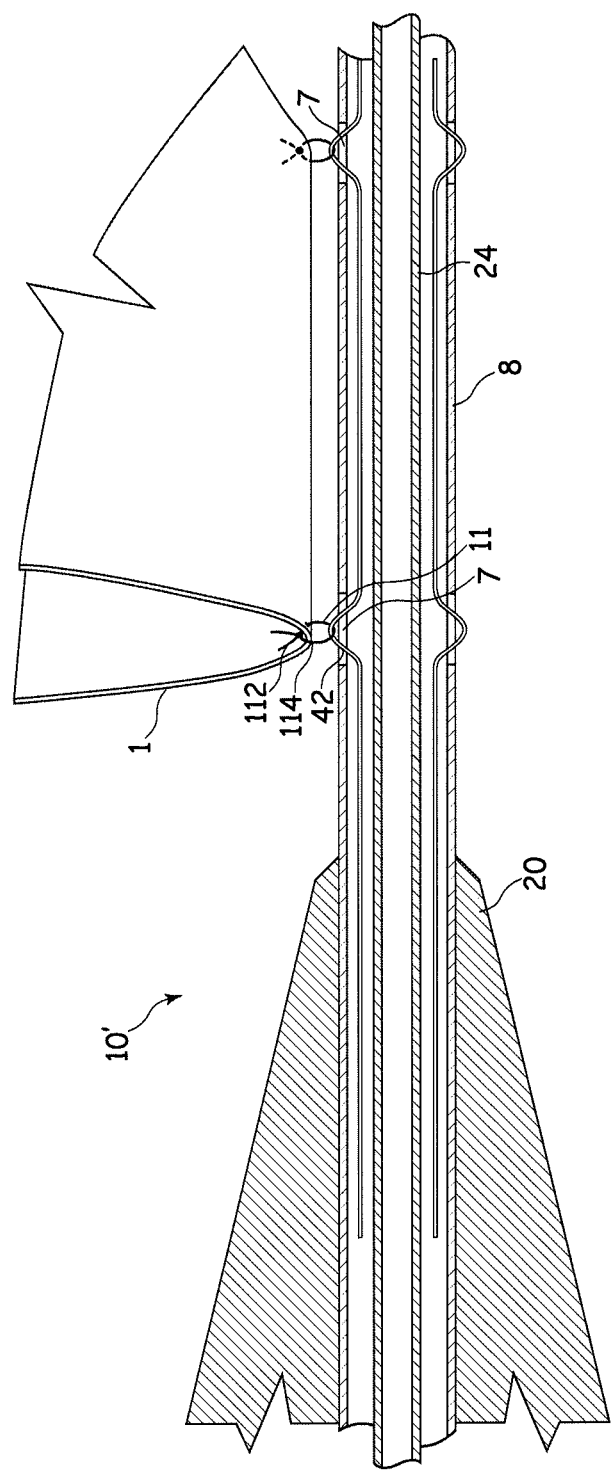
FIG. 9 shows a longitudinal cross-section through a portion of the deployment device shown in FIG. 5.

FIGS. 8 and 9 illustrate one example of a constraining mechanism for constraining the proximal stent 4' of a stent graft 18 on an introducer 10'. The deployment device 10' in the region of the proximal retention mechanism has, in this embodiment, a guide wire carrier 24 and a restraining wire carrier 8 (typically the carrier of the introducer for carrying the medical device) located coaxially around the guide wire carrier 24, that is such that the guide wire carrier resides in a lumen of the carrier 3 or 8. In some embodiments the guide wire may be located directly in the restraining wire carrier 8, thus avoiding the need for a separate guide wire carrier 24.

Restraining wires 42 pass along the annular space between the guide wire carrier 24 and the restraining wire carrier 8 and exit through apertures 7 at the six retention points and then re-enter the annular space between the guide wire carrier 24 and the restraining wire carrier 8 and pass into the nose cone dilator 20 to be secured thereby. A guide wire passes through the lumen of the guide wire carrier, catheter or cannula 24 in conventional manner.

In this embodiment, three separate restraining wires 42 are provided. Each restraining wire 42 extends to, and acts to constrain, an aligned proximal and distal attachment point on the proximal stent 4'.

The apertures 7 may be equally spaced around the restraining wire carrier 8 or they may be spaced at other selected spacings. In this embodiment there are two sets of three apertures 7 spaced at approximately 120° to each other around the circumference of and in pairs along the restraining wire carrier 8.

Where each restraining wire 42 exits out of an aperture 7, a thread of suture material or other thread-like material 11 is looped around the restraining wire 42 and is fastened to a bight 114 of the graft material 1 of the stent graft 18 and tied off with a knot 112. The restraining wires 42 extend to an external manipulation section 12 including a restraining wire actuation section 50, such as that illustrated in FIGS. 3 and 4.

In use, in order to improve the positioning of the stent graft 18 within a curved lumen, the constraining mechanism for the proximal stent 4' is only released after the remainder of the stent graft 18 has been expanded. This is described with reference to FIGS. 10 to 12.

It can be seen that the aortic or thoracic arch 130 of aorta 25 has an outer curve 33 and an inner curve 31. A stent graft 18 is deployed into the thoracic arch 130 to span, for instance, a tear 126 in the wall of the aorta 25 which has caused an aortic dissection 27.

Figure 10:
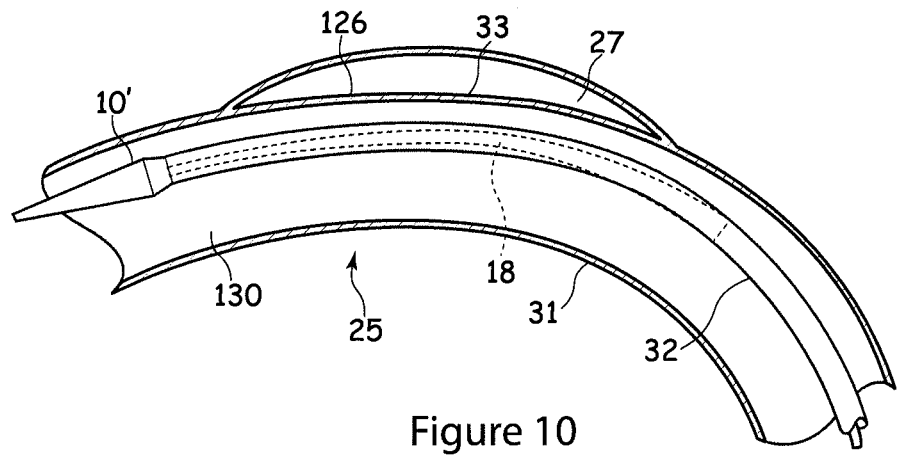
FIGS. 10 to 12 illustrate deployment of the stent graft of FIG. 5.

An introducer 10', having a stent graft 18 mounted thereon, is inserted into the aorta 25 and curved around the thoracic arch 130 as it passes through this, until the stent graft 18 is located at the desired site of deployment. FIG. 10 shows the introducer 10' prior to withdrawal of the sheath 32, which covers the stent graft 18. The introducer 10' is then oriented within the vessel, such that one of the constrained portions of the proximal stent 4' is facing the inner part of the curve (as can be best seen with reference to FIG. 11). The orienting step is carried out in a known manner using, for example, radio-opaque markers (not shown), which may be located on the stent graft 18 and/or on the deployment device 10'.

The surgeon or clinician then withdraws the sheath 32 to expose the stent graft 18. The stent graft 18 is allowed to expand by means of its self-expanding stents 4, in this embodiment, or by means of a balloon expansion mechanism in the case of use of stents which are not self-expandable.

Figure 11:
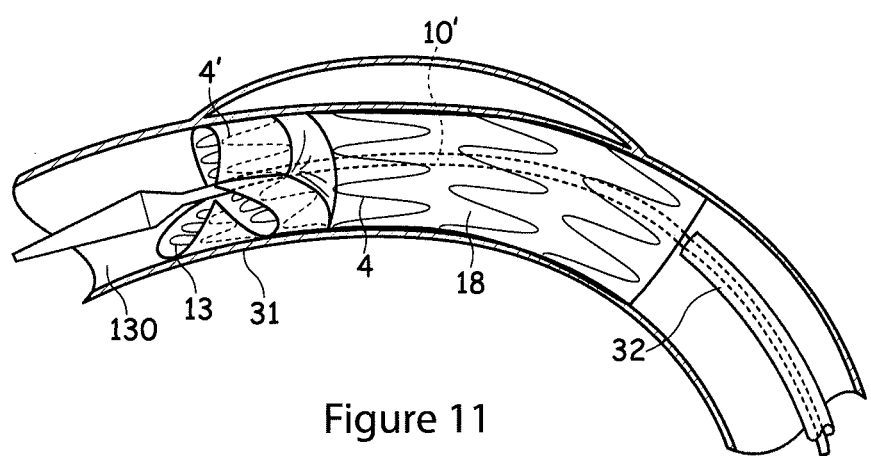
Figure 12:
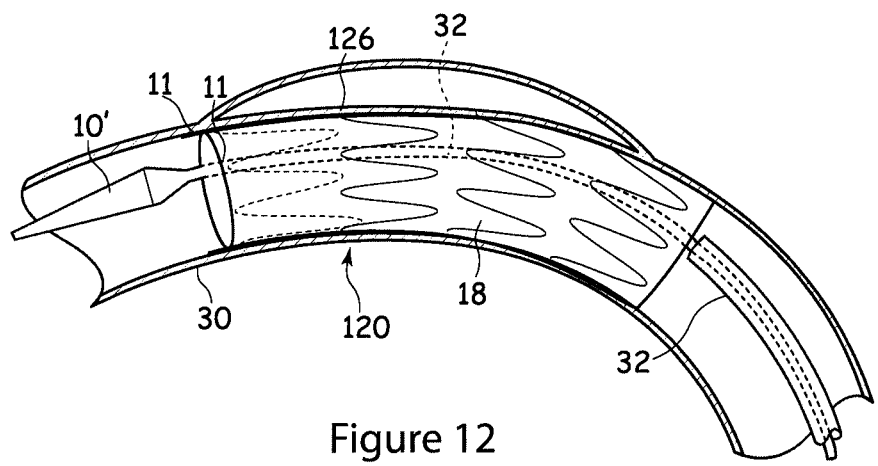

FIG. 11 shows the stent graft 18 after withdrawal of the sheath 32. It can be seen that the stent graft 18 has expanded apart from at the proximal stent 4', which is still constrained to the introducer 10' at three points around its circumference at both its proximal end and its distal end.

For the final stage of deployment, the surgeon or clinician releases the restraining wires 42 of the constraining mechanism to allow the proximal stent 4' to expand. The curve of the thoracic arch 130 forces the proximal stent 4' and its adjacent stent 4 closer together at the inner part of the curve 31. As the proximal stent 4' expands after its adjacent stent 4, the proximal stent 4' overlaps with the interior of its adjacent stent 4 at the inner part of the curve 31, forming a region of overlap 120.

This arrangement enables the plane of the proximal stent 4' to be positioned substantially perpendicularly to the vessel wall prior to release. As a result, it is possible to achieve an improved seal between the proximal stent 4' and the vessel wall. In prior art systems where the proximal stent is constrained only at its proximal end, the stent forms a cone shape after partial release, and is unable to be positioned perpendicularly to the vessel wall.

In this embodiment of FIGS. 5 to 12 it is important to orient the lobes of the proximal stent 4' in order to ensure that no lobe 13 becomes located on the inner side of the curve of the lumen, as so doing could prevent the stent 4' from overlapping into the second stent 4 as it is released and thus prevent proper positioning of the proximal stent 4'.

The skilled person will appreciate that modifications to the above-described embodiments may be made. In particular, the suture loops 11 may be provided on the proximal stent 4' or may be provided on the graft material 1. The constraining mechanism may be provided by any suitable arrangement. The above-described arrangement is merely exemplary. In some embodiments there could be provided six restraining wires, each able to restrain a single suture loop 114.

Figure 13:
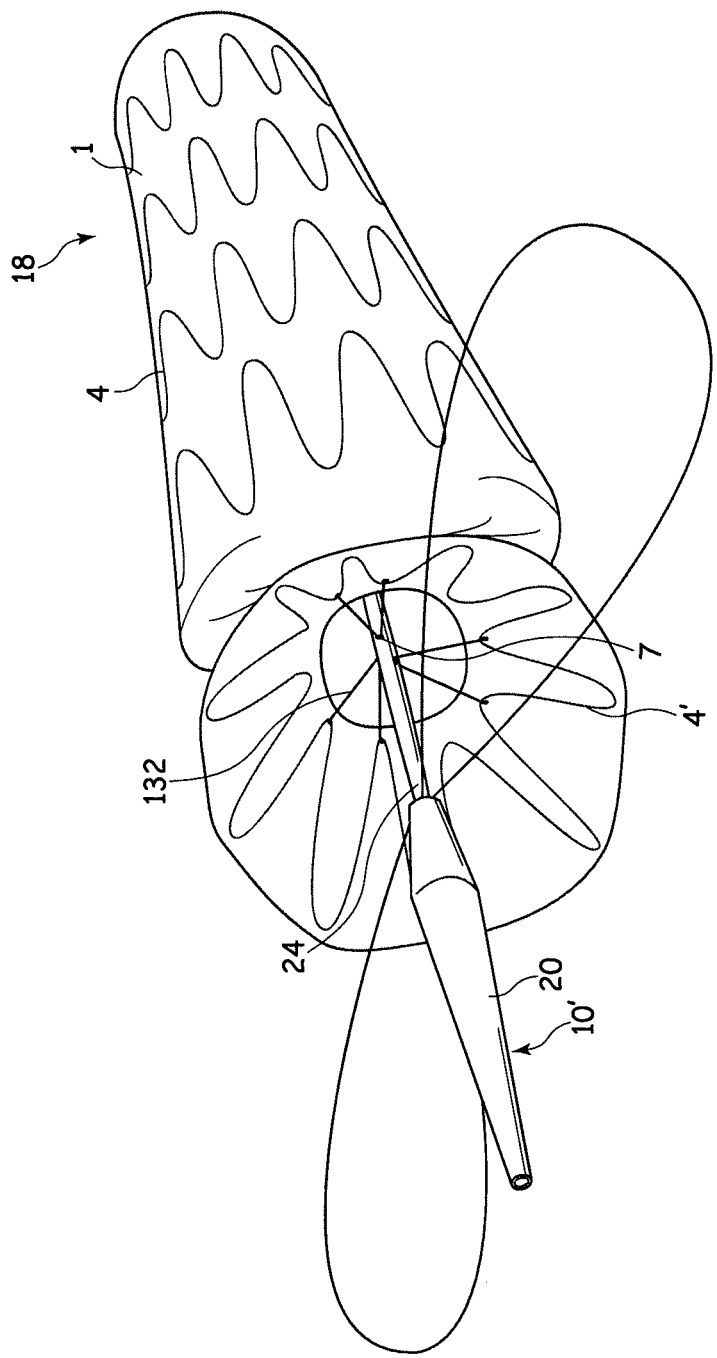
FIG. 13 illustrates another embodiment of a stent graft.
Figure 14:
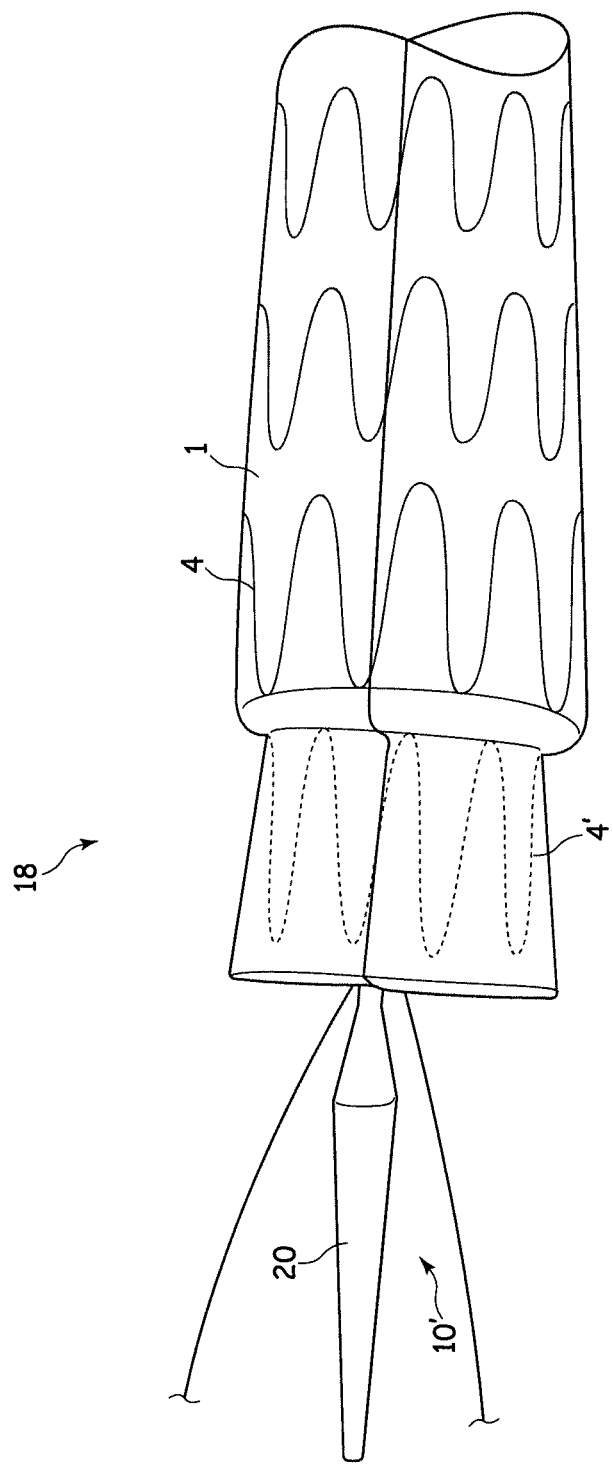
FIG. 14 illustrates another view of the stent graft of FIG. 13.
Figure 15:
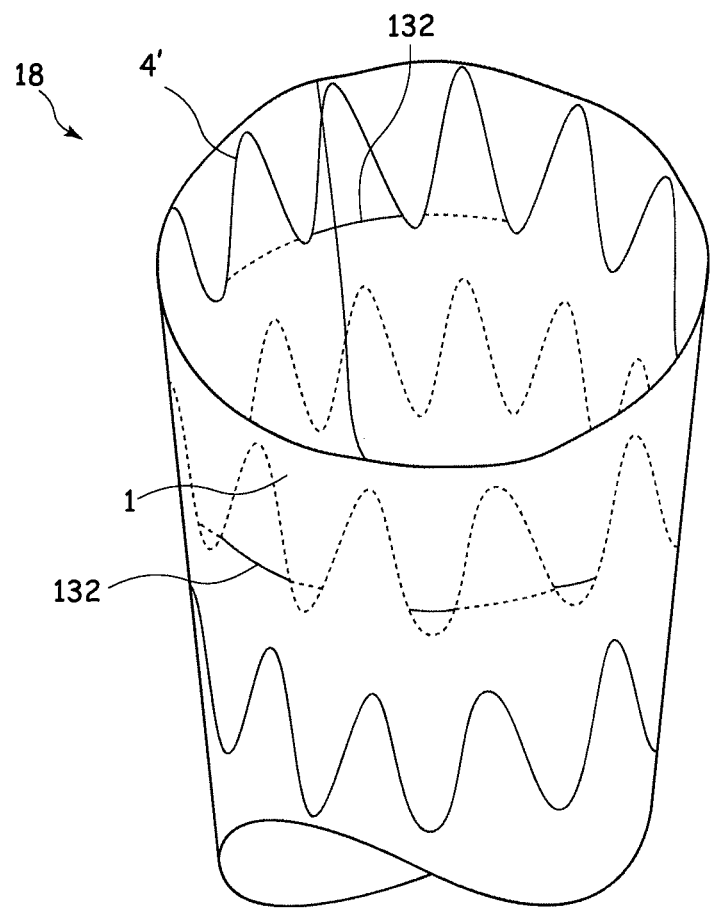
FIG. 15 illustrates another view of the stent graft of FIG. 13.

Another embodiment of a stent graft 18 for deployment within a curved lumen is described with reference to FIGS. 13 to 15, which shows a stent graft 18 having a proximal stent 4' that is to be constrained at both its proximal and distal ends during deployment. FIGS. 13 and 14 show the proximal stent 4' in its partially deployed state, that is after release of the proximal end of the proximal stent 4' but before its distal end has been fully released.

As can best be seen in FIG. 13, there is provided on the stent graft 18 a suture arrangement in which three suture loops 132 can be pulled into the center of the stent graft 18, that is towards the guide wire carrier 24 and held thereto by a release wire within the lumen of the guide wire carrier 24 through a plurality of openings 7 therein. The arrangement of suture loops 132 differs from the arrangement of the embodiment illustrated in FIGS. 5 to 9, in that a plurality of pairs of struts of the proximal stent 4' is constrained by each loop arrangement, thereby pulling the entirety of the distal end of the proximal stent 4' towards the guide wire carrier 24, as can be seen in FIGS. 13 and 14. It is preferred that the proximal stent 4' is still pulled in a tri-lobed configuration, as with the embodiment of FIGS. 5 to 9, but in such a way that the entirety of the distal end of the proximal stent 4' is pulled inwardly to some extent and thus to lie within the perimeter of the second stent 4 adjacent to it.

A variety of different embodiments of suture arrangements for the stent graft 18 are possible. One embodiment is shown in FIG. 15, in which there are provided three lengths of suture thread 132 each attached to four stent apices. Each suture thread 132 is located generally on the outside of the graft material 1 apart from a length which feeds to the inside of the graft material 1, as can best be seen in FIG. 15. This length can be fed through an opening 7 in the guide wire carrier 24 and restrained by a restraining wire therein, to produce the tied arrangement shown FIG. 13. A similar arrangement is provided also at the proximal end of the proximal stent 4' to constrain this to the guide wire carrier 24.

Although not shown in the Figures, it is preferred that three restraining wires are provided, extending through the guide wire carrier 24. Each restraining wire can then serve to engage generally aligned proximal and distal suture threads 132. It will be appreciated that the proximal and distal constraining mechanisms may be slightly off-set with respect to one another due to the nature of the Z-stents used in this example.

Deployment of this embodiment is very similar to that described above with respect to FIGS. 10 to 12. The main difference is that orientation of the stent graft 18 with respect to the curvature of the vessel is not required. The reason for this is that since the entirety of the circumference of the distal end of the proximal stent 4' is pulled inwardly towards the carrier 3 or 24. Thus, as the stent graft is deployed, the distal end of the proximal stent 4' is already in partial overlap with the second stent 4 of the stent graft and thus better able to conform to the curvature of the vessel. This therefore renders deployment more straightforward.

As illustrated in FIGS. 13 and 14, it is also preferred that withdrawal of the release wires engaged with the suture threads 132, acts firstly to release the proximal end of the proximal stent 4' and secondly to release the distal end of the proximal stent 4'.

It can be seen from the above that in this embodiment, the constraining mechanism constrains the distal end of the most proximal stent 4' substantially around the entirety of its circumference yet preferably still retaining a tri-folded configuration. As is apparent from FIG. 14, the distal end of the proximal stent 4' lies within the circumference of the second stent 4 and, when deployed in a curved lumen, will expand to overlap with the interior of the second stent 4 so as to follow more accurately the curvature of the lumen (aortic arch). This results in an improved fit within the patient's lumen.

Pulling the distal end of the proximal stent 4' to the carrier 24 has another important advantage in that the stent graft 18 is then held to the guide wire carrier 24 during deployment. When in the aortic arch, the introducer 10, and thus the guide wire carrier 24, will tend to follow the outside of the curve of the aortic arch, that is, the region of greater length. Thus, the stent graft 18 will be urged against the lumen wall at the outside of the curve with those parts at the inside of the curve held away from the vessel wall by being held close to the guide wire carrier 24. Thus, the portions of the stent graft 18 which will be positioned on the shorter part of the inside of the curve will only come into contact with this once they are released from the guide wire carrier 24 and thus already in a curved configuration. This assists in ensuring that the distal end of the proximal stent 4' on the inside of the curve overlaps with the proximal end of the second stent thereby to provide good conformity with the vessel wall.

The skilled person will appreciate that there are of course many modifications that could be made to this embodiment.

Figure 16:
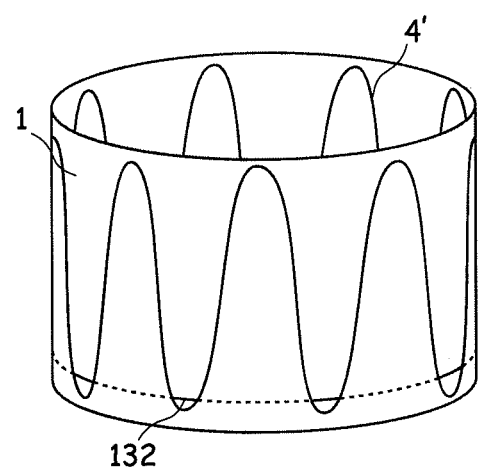
FIG. 16 illustrates a modified arrangement of suture threads that may be used with the stent graft of FIG. 13.

In a modification, one or more suture threads 132 may be located preferably substantially entirely on the outside of the graft layer 1 in order to minimize the amount of suture material 132 on the inside thereof which could interfere with medical devices subsequently introduced through the stent graft, such as during a subsequent medical procedure. FIG. 16 illustrates such a modification, in which portions of suture thread located on the outside of the graft material are shown as a dashed line, while portions of suture thread 130 on the inside of the graft material 1 are shown as a thicker solid line. It can be seen that suture material 132 is located on the inside of the graft material 1 only between the struts of the proximal stent 4', and towards the apices thereof. In this way, the struts act to hide or shield the loops of suture material 132 from any later used medical device. The suture threads 132 are thus somewhat protected by the struts of the proximal stent 4' from snagging on a later inserted medical device.

FIG. 16 shows the use of a single length of suture material 130 circumscribing the entirety of the circumference of the stent graft 1. This facilitates the manufacture of the stent graft 1 as well as facilitating its mounting onto an introducer, in particular in cases where there are provided many portions 132 of suture material extending into the inside of the graft tube and thus each being selectively able to be held by the constraining wires. On the other hand, there could be provided separate lengths of suture material, as in the embodiment of FIG. 15, but in which the portion 132 extending into the graft tube is located between the apex (trough when viewed as in FIG. 15) of two stent struts in order to provide the shielding described above.

In the preferred embodiment (as described above), three restraining wires are used, one for each suture thread 132, but each engaging with both a proximal and a distal suture thread 132. However, it is possible to use only a single restraining wire, which engages with all three suture threads 132, though this arrangement may interfere with the position of the guide wire. In another modification, six restraining wires may be used, each engaging with a single proximal or a single distal suture thread 132. An advantage of this embodiment is that it allows improved control of release of the proximal stent 4'.

It is to be appreciated that the proximal end of the proximal stent 4' is preferably retained by a similar arrangement of suture threads 130 such that when the stent graft is first deployed the proximal stent 4' is held both at its proximal and at its distal ends by the constraining mechanisms in, preferably, a tri-lobed manner but in which the lobes do not extend beyond the diameter of the second stent 4. During deployment, once the remainder of the stent graft 1 has been deployed, the proximal end of the stent 4' is released, allowing the proximal end to open up in a manner as shown in FIGS. 13 and 14 in particular. This allows the proximal end of the stent graft 1 to engage the walls of the patient's vessel and to be held thereto, particularly in the case where fixing barbs are provided. Then, the distal end of the stent 4' can be released, allowing this to expand and in particular allowing the distal end of the stent 4' at the inside of the curve to expand in overlapping manner into the second stent 4. This can ensure good curvature of the stent graft 1 particularly at its proximal end and thus better conformity with the vessel wall and better sealing.

What has been described and illustrated herein is a preferred embodiment of the invention along with some of its variations. The terms, descriptions and figures used herein are set forth by way of illustration only and are not meant as limitations. Those skilled in the art will recognize that many variations are possible within the spirit and scope of the invention, which is intended to be defined by the following claims, and their equivalents, in which all terms are meant in their broadest reasonable sense unless otherwise indicated.

The disclosures in United Kingdom patent application 0820061.0, from which the present application claims priority, and in the abstract accompanying this application are incorporated herein by reference.

We claim:

1. An introducer for deploying a stent graft in a curved lumen, the introducer comprising:
   a stent graft having an internal lumen, and a carrier for the stent graft, the stent graft disposed over the carrier for the stent graft;
   the stent graft comprising a tube of graft material, a proximal stent at a proximal end of the stent graft entirely overlapping the graft material of the tube of graft material, and a distally adjacent stent, the proximal stent having a proximal end having a plurality of proximal apices and a distal end having a plurality of distal apices, wherein each of the proximal and distal ends of the proximal stent have a constrained circumference and an expanded circumference;
   a first constraining mechanism configured to maintain the proximal end of the proximal stent at a partially constrained circumference on the carrier;
   a second constraining mechanism configured to maintain the distal end of the proximal stent at a partially constrained circumference such that the distal end of the proximal stent is pulled inwardly towards the carrier, wherein the second constraining member comprises at least one thread that extends about the entire circumference of the stent graft such that first lengths of the at least one thread extend partially circumferentially about an exterior of the tube of graft material at a plurality of points and second lengths of the at least one thread extend through the graft material and at least partially circumferentially about an interior of the tube of graft material at a plurality of points to form a plurality of inwardly extending loops of thread within the internal lumen between the distal end of the proximal stent and the carrier such that the distal end of the proximal stent is pulled toward the carrier from the interior of the tube of graft material,
   one or more longitudinally extending wire release mechanisms engaging the constraining mechanisms,
   wherein each of the plurality of loops of the second constraining member engages one or more of the longitudinally extending wire release mechanisms; and
   wherein the longitudinally extending wire release mechanisms are configured to release the proximal end of the proximal stent to the expanded circumference prior to the release of the distal end of the proximal stent to the expanded circumference.

2. The introducer of claim 1, wherein the longitudinally extending wire release mechanism includes at least three longitudinally extending wires.

3. The introducer of claim 1, wherein at the constrained circumference the proximal end of the proximal stent is pulled inwardly towards the carrier at at least two points each to form substantially equally sized lobes.

4. The introducer of claim 1, wherein at the constrained circumference the proximal end of the proximal stent is pulled inwardly towards the carrier at at least three points each to form substantially equally sized lobes.

5. The introducer of claim 1, wherein each of the loops of threads are disposed at a distal apex of the plurality of distal apices between two struts that form the apex.

6. The introducer of claim 1, wherein the first lengths of the thread that extend partially circumferentially about the exterior of the tube of graft material extend at least partially between struts of adjacent distal apices.

7. The introducer of claim 6, wherein the second lengths of the thread that extend partially circumferentially about the interior of the tube of graft material extend at least partially between struts of adjacent distal apices.

8. The introducer of claim 6, wherein the first lengths of the thread that extend partially circumferentially about the exterior of the tube of graft material each extend over a strut of a first distal apex to a next adjacent strut of a second distal apex and over the next adjacent strut and through the graft material.

9. The introducer of claim 1, wherein the at least one thread comprises a single length of thread circumscribing the entire circumference of the distal end of the proximal stent substantially entirely on the outside of the stent graft and only extends partially within the inner lumen of the stent graft at the plurality of apices.

10. An introducer for deploying a stent graft in an at least partially curved lumen, the introducer comprising:
    a stent graft comprising a tube of graft material and having an internal lumen, and a carrier for the stent graft, the stent graft disposed over the carrier;
    the stent graft comprising a proximal stent at a proximal end of the stent graft and a distally adjacent stent;

the proximal stent having a proximal end having a constrained circumference and an expanded circumference and a distal end having a constrained circumference and an expanded circumference;
a first constraining mechanism constraining the proximal end of the proximal stent at the constrained circumference;
a second constraining mechanism constraining the distal end of the proximal stent at the constrained circumference such that the entire circumference of the distal end is pulled inwardly towards the carrier;
at least one trigger wire release mechanism engaging the constraining mechanisms, the at least one trigger wire release mechanism configured to release firstly the proximal end of the proximal stent and secondly the distal end of the proximal stent to the expanded circumference,
wherein the second constraining member comprises at least one thread that extends circumferentially about the distal end of the proximal stent for a plurality of lengths exterior to the stent graft and a plurality of lengths interior to the stent graft, and
wherein the plurality of lengths interior to the stent graft comprise a plurality of loops within the internal lumen with each loop disposed at a distal apex between adjoining struts of the distal apex, and extending between the distal apex and the carrier such that the distal end of the proximal stent is pulled toward the carrier from the interior of the tube of graft material,
wherein each of the plurality of loops of the second constraining member engage one or more of the trigger wire release mechanisms.

11. The introducer of claim 10, wherein the first constraining mechanism constrains the proximal end of the proximal stent at at least three points to form at least three lobes.

12. The introducer of claim 11, wherein the first constraining mechanism comprises a loop of thread at each point with each loop of thread engaging one of the points and engaging the carrier.

13. The introducer of claim 10, wherein the plurality of lengths that extend about the external surface each extend over a strut of a first distal apex, across a span of graft material between a next adjacent distal apex, and over a strut of the next adjacent distal apex.

14. The introducer of claim 10, where the plurality of loops includes at least three equally spaced loops about the interior of the stent graft.

15. A stent graft for deployment in a curved lumen, including:
a graft material providing an inner lumen;
a plurality of stents located longitudinally along the graft material, the plurality of stents comprising a proximal stent located at a proximal end of the stent graft and disposed entirely within the inner lumen of the graft material, the proximal stent having a proximal end and a distal end and proximal apices and distal apices;
the plurality of stents having an expanded circumference and a constrained circumference;
a first constraining mechanism engaging the proximal apices of the proximal stent, and configured to constrain the proximal end of the proximal stent at the constrained circumference; and
a second constraining mechanism engaging the distal apices of the proximal stent to constrain the distal end of the proximal stent at a partially constrained circumference, while a portion of the stent graft distal to the proximal stent is at the expanded circumference, wherein the second constraining mechanism constrains substantially the entire circumference of the distal end of the proximal stent;
the stent graft having a curved configuration in the constrained configuration wherein the stent graft has an inside curve and the distal end of the proximal stent, when in the constrained circumference, lies partially inside the expanded circumference of a distally adjacent stent,
wherein the second constraining member comprises at least one thread that extends partially circumferentially about an exterior of the tube of graft material, extends through the graft material, extends at least partially circumferentially about an interior circumference of the graft material, and forms a plurality of loops within the inner lumen,
wherein each loop of the plurality of loops extends between struts that are adjacent the same apex, such that the distal end of the proximal stent is pulled toward the interior of the tube of graft material, and wherein the loops are spaced at equal intervals about the interior circumference of the stent graft.

16. The stent graft of claim 15 in combination with a stent graft carrier, wherein the stent graft is disposed on the carrier and in the constrained circumference the proximal end of the proximal stent is pulled inwardly towards the carrier at at least two points each to form at least two lobes extending away from the carrier.

17. The stent graft of claim 15 in combination with a stent graft carrier, wherein the plurality of loops consists of four loops spaced equally about the interior of the draft material.

18. An introducer for deploying a stent graft in a curved lumen, the introducer comprising:
a carrier having a stent graft retention region with the stent graft disposed over the stent retention region;
the stent graft comprising a tube of graft material having an internal lumen, a proximal stent at a proximal end of the stent graft and not extending beyond the proximal end of the stent graft, and a plurality of stents disposed on the stent graft distal to the proximal stent, the proximal stent having a proximal end and a distal end having distal apices, wherein each of the proximal and distal ends have a constrained circumference and an expanded circumference;
a first constraining mechanism attaching the proximal end of the proximal stent to the carrier and holding the proximal end of the proximal stent at a partially constrained circumference;
a second constraining mechanism attaching the distal end of the proximal stent to the carrier and holding the distal end of the proximal stent at the constrained circumference such that the distal end of the proximal stent is pulled fully inwardly towards the carrier;
one or more trigger wire release mechanisms engaging the constraining mechanisms, the release mechanisms configured to release the proximal end of the proximal stent to the expanded circumference prior to the release of the distal end of the proximal stent to the expanded circumference;
wherein the second constraining member comprises at least one thread that extends partially about the entire circumference of the distal end of the proximal stent and extends circumferentially about an exterior of the tube of graft material, extends through the graft material, extends at least partially circumferentially about an interior of the tube of graft material, and forms a plurality of loops within the internal lumen each at an apex of the plurality of distal apices, and extends between those distal apices of the plurality of apices and the carrier such that the distal end of the proximal stent is pulled toward the carrier from the interior of the tube of graft material, wherein each of the plurality of loops of the second constraining member engage one or more of the trigger release mechanisms.

* * * * *

UNITED STATES PATENT AND TRADEMARK OFFICE
CERTIFICATE OF CORRECTION

| | |
|---|---|
| PATENT NO. | : 10,675,140 B2 |
| APPLICATION NO. | : 15/839115 |
| DATED | : June 9, 2020 |
| INVENTOR(S) | : Tilo Kölbel et al. |

Page 1 of 1

It is certified that error appears in the above-identified patent and that said Letters Patent is hereby corrected as shown below:

In the Claims

Column 14, Claim 17, Line 32, delete "draft" and replace with --graft--.

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*